(12) United States Patent
Dastych et al.

(10) Patent No.: US 9,476,086 B2
(45) Date of Patent: Oct. 25, 2016

(54) **BACTERIOPHAGE WITH ACTIVITY AGAINST PATHOGENIC STRAINS OF *SALMONELLA***

(75) Inventors: Jarosław Dastych, Łódź (PL); Jarosław Dziadek, Łódź (PL); Elżbieta Górecka, Łódź (PL); Anna Rumijowska-Galewicz, Łódź (PL); Arkadiusz Wojtasik, Łódź (PL); Ewelina Wójcik, Łódź (PL)

(73) Assignee: PROTEON PHARMACEUTICALS S.A., Lodz (PL)

( * ) Notice: Subject to any disclaimer, the term of this patent is extended or adjusted under 35 U.S.C. 154(b) by 0 days.

(21) Appl. No.: 14/240,195

(22) PCT Filed: Aug. 9, 2012

(86) PCT No.: PCT/IB2012/054070
§ 371 (c)(1),
(2), (4) Date: Mar. 14, 2014

(87) PCT Pub. No.: WO2013/027146
PCT Pub. Date: Feb. 28, 2013

(65) Prior Publication Data
US 2014/0220659 A1    Aug. 7, 2014

(30) Foreign Application Priority Data
Aug. 25, 2011   (PL) .......................... 396080

(51) Int. Cl.
*A61K 35/76* (2015.01)
*A23K 10/18* (2016.01)
*A23K 50/75* (2016.01)
*C12N 7/00* (2006.01)
*C12Q 1/18* (2006.01)

(52) U.S. Cl.
CPC ............. *C12Q 1/18* (2013.01); *A23K 10/18* (2016.05); *A23K 50/75* (2016.05); *A61K 35/76* (2013.01); *C12N 7/00* (2013.01); *C12N 2795/00021* (2013.01); *C12N 2795/00032* (2013.01)

(58) Field of Classification Search
None
See application file for complete search history.

(56) References Cited

U.S. PATENT DOCUMENTS 5,824,468 A    10/1998  Scherer et al.
2011/0052544 A1    3/2011  Shin et al.

FOREIGN PATENT DOCUMENTS

| SU | 543260 A | 4/1984 |
| WO | WO 01/00786 A2 | 1/2001 |
| WO | 03054173 A1 | 7/2003 |
| WO | 03103578 A2 | 12/2003 |

OTHER PUBLICATIONS

Capparelli et al., The Journal of Infectious Diseases, 2009, 201:52-61.*
Application of Probiotics in Poultry Production, Martin Kral, Maria Angelovicova, Lubica Mrazova; Slovak University of Agriculture in Nitra, Faculty of Biotechnology and Food Sciences, Department of Food Hygiene and Safety, 949 76-Nitra, Tr. A. Hlinku, 2, Slovakia, 2012; Animal Science and Biotechnologies, 2012, 45 (1).
Search Report for PL 396080 dated Oct. 5, 2011.
Selection and Application for Bacteriophages for Treating *Salmonella enteritidis* Infections in Poultry, International Journal of Poultry Science 6(3): 163-168, 2007, S.E. Higgins, J.P. Higgins, L.R. Bielke and B.M. Hargis, Department of Poultry Science, University of Arkansas, Fayetteville, AR 72701, USA, 2007.
L.R. Bielke, T. Tellez and B.M. Hargis (2012). Successes and Failures of Bacteriophage Treatment of Enterobacteriaceae Infections in the Gastrointestinal Tract of Domestic Animals, Dr. Ipek Kurtboke (Ed.), ISBAN: 978-953-51-0272-4, InTech.
Physicochemical Properties of Bacteriophages: II. Sedimentation of Bacteriophage T6. Frank W. Putnam, Journal of Biological Chemistry 1951, 190:61-74.
Dooley, "Rapid visualization of the results of staphylococcal bacteriophage typing", Military Medicine, 1962, pp. 399-404, vol. 121, Nr: 5, Association of Military Surgeons of the US, Bethesda, MD, US—ISSN 0026-4075.

* cited by examiner

*Primary Examiner* — Nicole Kinsey White
(74) *Attorney, Agent, or Firm* — Law Office of Salvatore Arrigo and Scott Lee, LLP

(57) ABSTRACT

A method for obtaining a strain of bacteriophage specific to a selected strain of bacteria was found as well as bacteriophage strains obtained in this way. Moreover, application of bacteriophages in manufacturing of the preparation for preventing and fighting infections of farm animals, especially poultry, with pathogenic strains of bacteria sensitive to these phages was described.

9 Claims, 7 Drawing Sheets

BACTERIOPHAGE WITH ACTIVITY AGAINST PATHOGENIC STRAINS OF *SALMONELLA*

Figure 1:
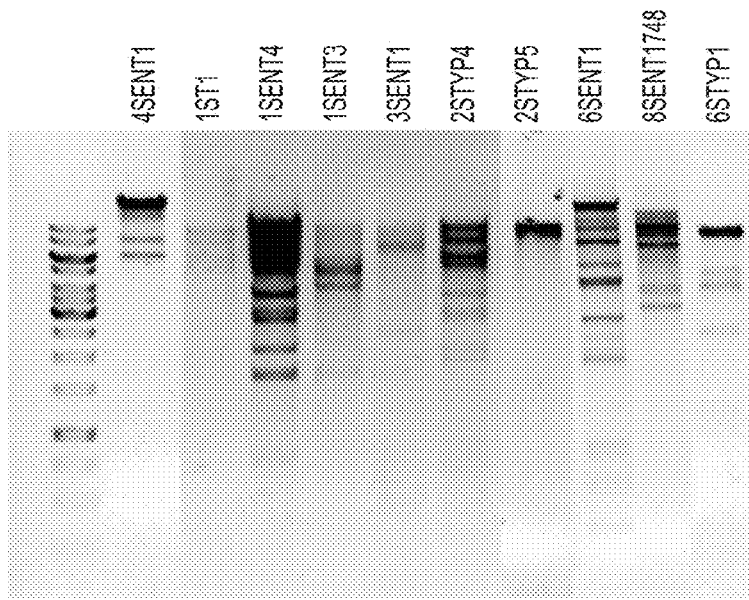

This invention relates to a method for preparing a strain of bacteriophage specific to a selected strain of bacteria, bacteriophage strains obtained in this way and the application of bacteriophages to manufacture preparation for preventing and fighting infections of farm animals, especially poultry, with pathogenic strains of bacteria sensitive to these bacteriophages.

The aim of the invention is to provide production technology for an antimicrobial preparation suitable for use as a feed additive for poultry and pigs, which at the same time would be specific to pathogenic strains of *Salmonella* spp that cause incidence of salmonellosis, especially in humans. The preparation shall comply with strict safety requirements for feed additives. Prohibition to use antibiotics in animal feed, valid in European Union countries since 1 Jan. 2006, created a huge demand for feed additives, not containing antibiotics, but having anti-microbial effect.

The aim of the present invention is to provide a preparation that could replace the currently used antibiotics.

Unexpectedly, such preparation was successfully obtained in the present invention.

This invention relates to a method of preparing a strain of bacteriophage specific to a selected strain of bacteria, characterized in that:
a) a collection of bacteriophage strains containing a strain of bacteriophage specific to a selected strain of bacteria is obtained,
b) culture of a selected strain of bacteria on a sterile culture medium is conducted,
c) the culture samples are applied on the special multi-well measuring plate, then a suspension of tested bacteriophage strain at various concentrations is added and it is incubated at 37° C. for at least 4 hours,
d) resazurin is added to the culture and the incubation is continued in the dark at 37° C., for at least 3 hours,
e) the colour or fluorescence of culture is being controlled, as well as bacteriophage strain contained in the culture that retains the blue colour or shows no significant increase in fluorescence compared with the control sample, is identified as a strain of bacteriophage specific to a selected strain of bacteria. A sterile sample that was treated with the same incubation is used as a control sample,
f) identified strain of bacteriophage specific to a selected strain of bacteria is propagated.

Favourably, the selected bacterial strain is a strain of *S. enterica* serovar Enteritidis.

The disclosed method is suitable for an easy and rapid screening of large collections of bacteriophage and allows for easy determination of the titre (lytic strength) of tested phages, which is essential in industrial applications.

Another object of the invention is the use of bacteriophages to manufacture a preparation for preventing and fighting infections of farm animals, especially poultry, with pathogenic strains of bacteria sensitive to these bacteriophages. The manufactured preparation is intended to be administered to endangered animals with food or water, at intervals of one to seven days.

Favourably, the manufactured preparation provides at least 200-fold reduction in the level of infection a week after the administration is stopped.

Favourably, the infection to be fought is an infection of poultry with pathogenic strains of *Salmonella* sp., whereas in order to manufacture the preparation, a bacteriophage strain is selected from the group consisting of those strains disclosed in this application, deposited on 7 Jun. 2011, in the Polish Collection of Microorganisms, under the following deposit numbers: PCM F/00069 (strain 8 sent 1748), PCM F/00070 (strain 8 sent 65) and PCM F/00071 (strain 3 sent 1), is used.

Another object of the invention is a strain of bacteriophage suitable to prevent or fight infections by pathogenic strains of *Salmonella* sp., selected from the group consisting of: PCM F/00069 (strain 8 sent 1748), PCM F/00070 (strain 8 sent 65) and PCM F/00071 (strain 3 sent 1).

The preparation according to the invention is based on natural components of the ecosystem and has no unfavourable influence on organisms other than specific pathogenic bacteria. While commercially available substitutes of antibiotics are based on substances which, like for example, organic acids, non-specifically modulate the bacterial flora, preventing to some extent the growth of undesirable microorganisms, the preparation according to the invention ensures that only pathogenic strains of *Salmonella* spp are selectively reduced. Unexpectedly, it also appeared that the preparation according to the invention is not maintained in the human or animal body, if there is no *Salmonella* spp present. In a particular realization, the preparation is suitable for use in animal production, especially to fight *Salmonella* infection in poultry.

Bacteriophage strains disclosed in this application were identified by a process according to the invention. Unexpectedly, they show a wide specificity involving the lysis of at least four specific serotypes of *Salmonella* and maintain to be stable in refrigerated storage conditions for at least 3 months. Moreover, they can be successfully propagated on an industrial scale without loss of activity and they are not specific to the pro-biotic *Lactobacillus* bacteria.

Figure 3:
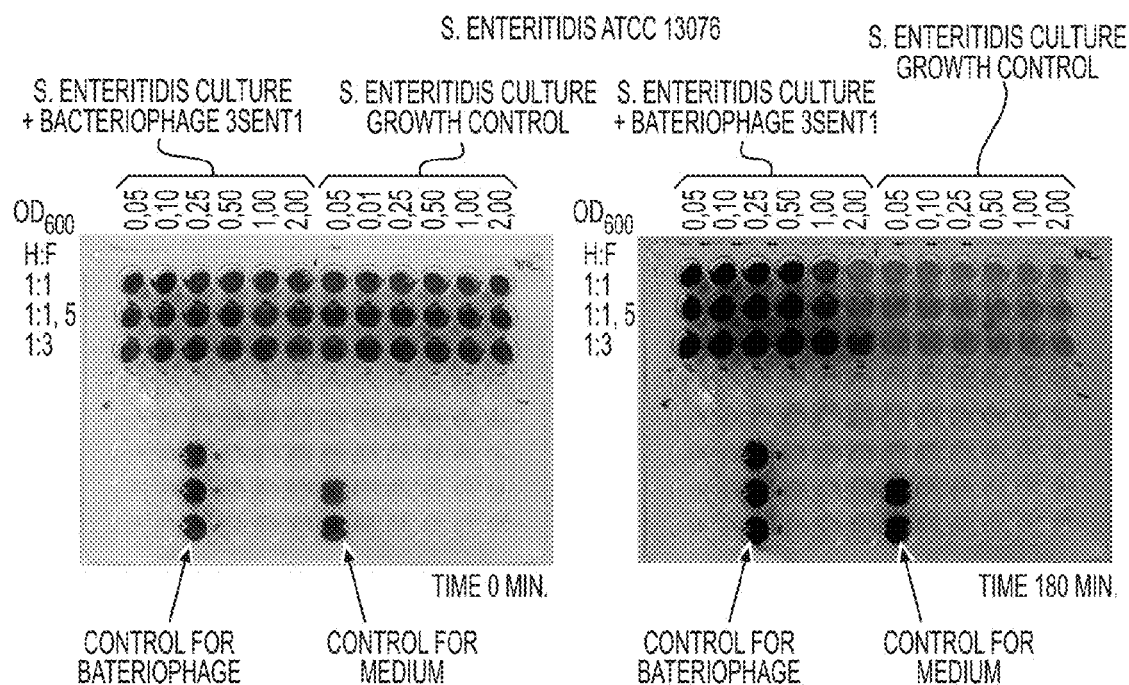
Figure 2:
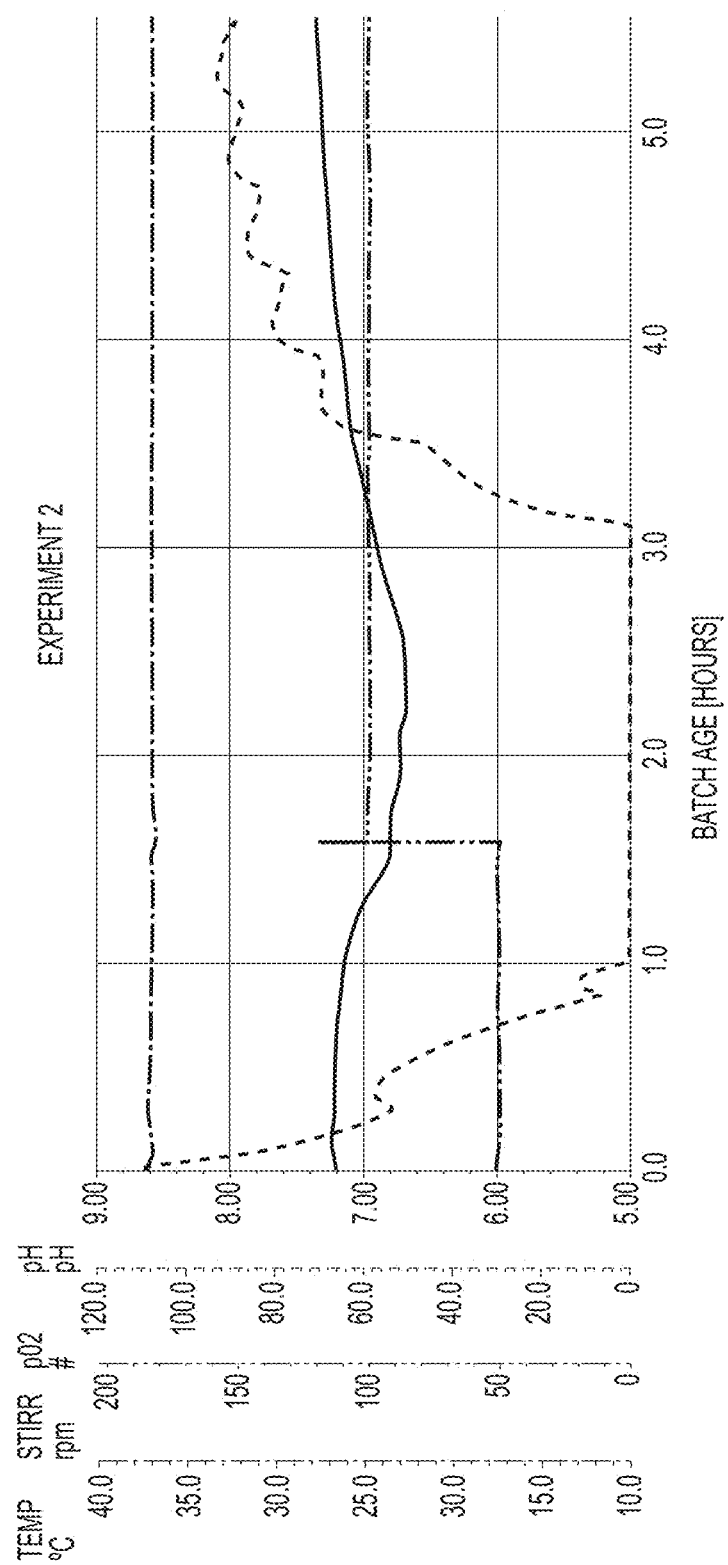
Figure 2:
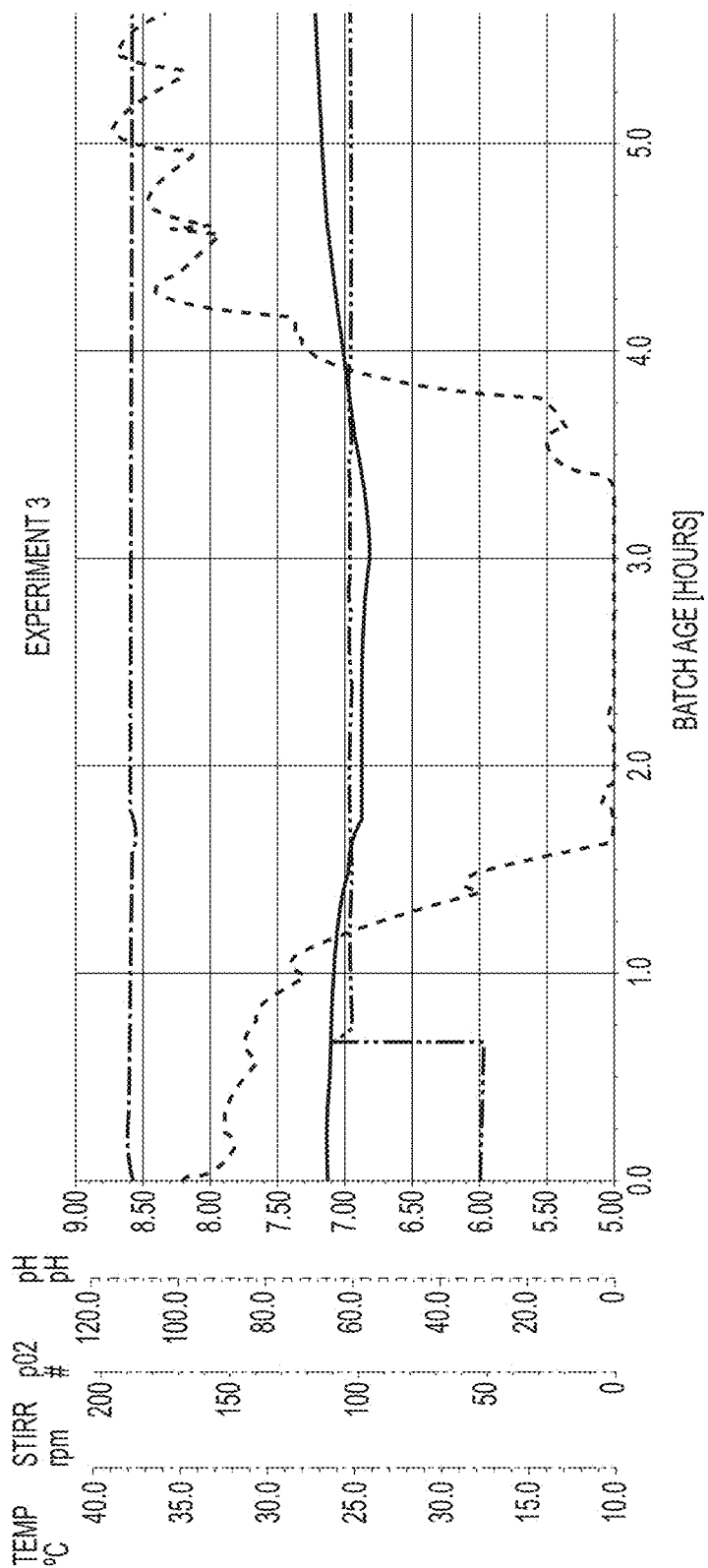
Figure 2:
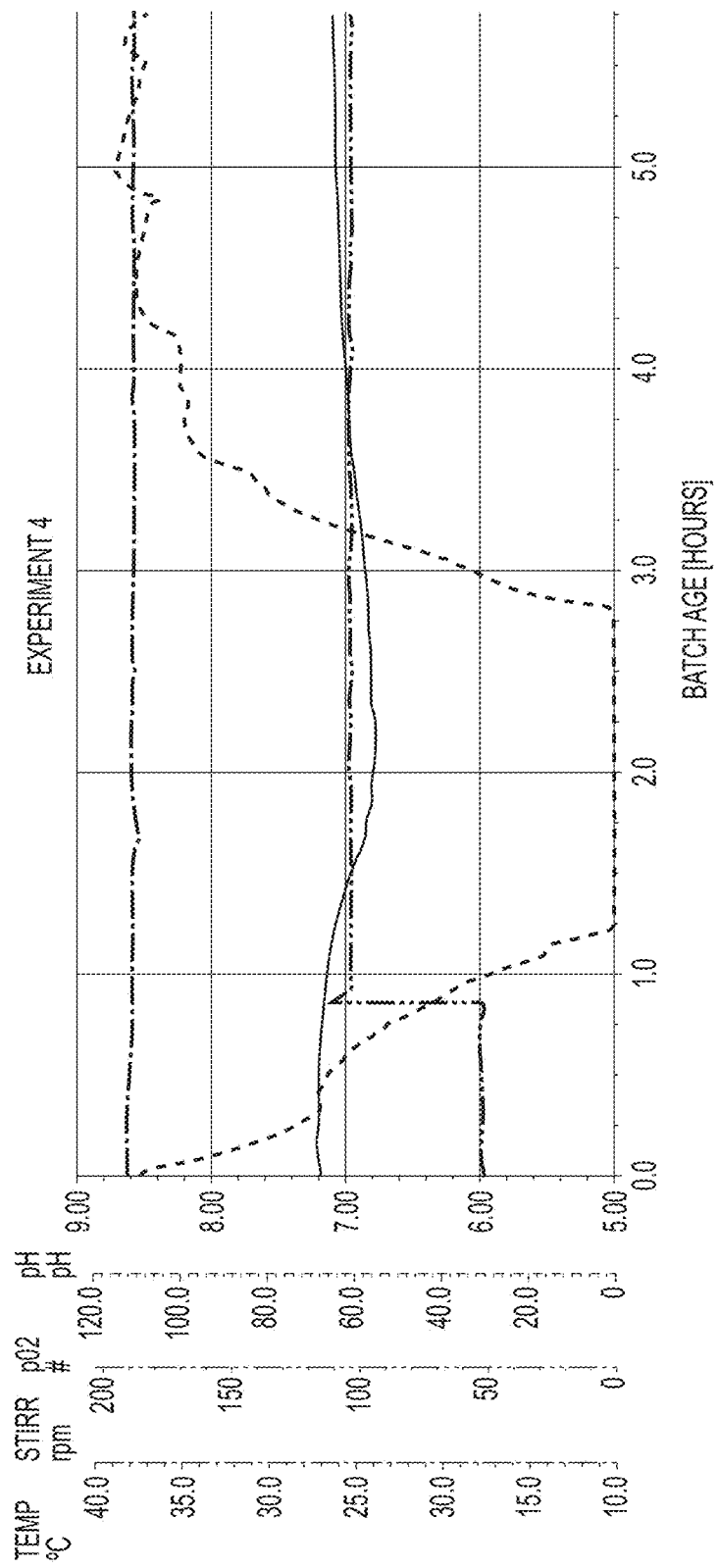
Figure 4:
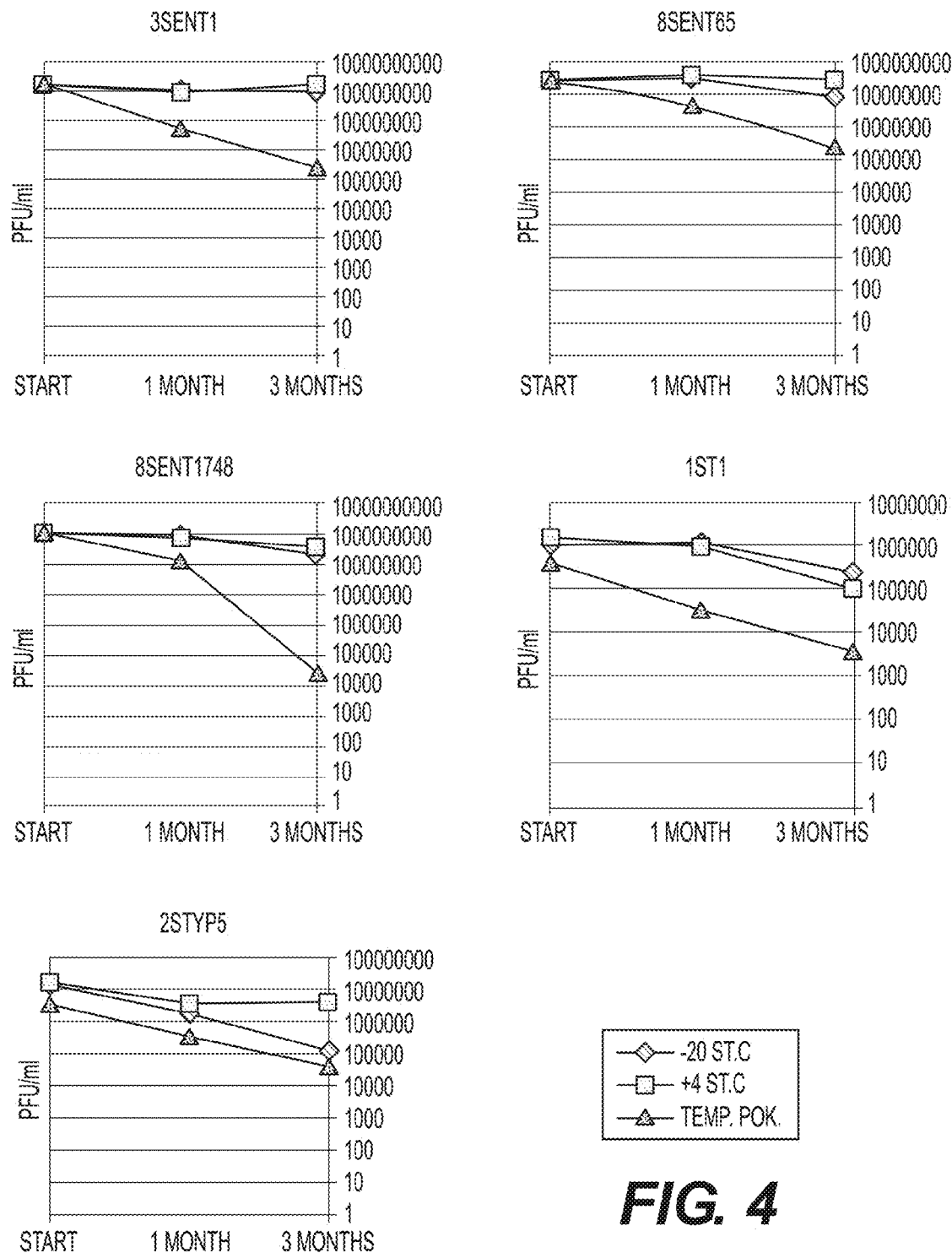
Figure 5:
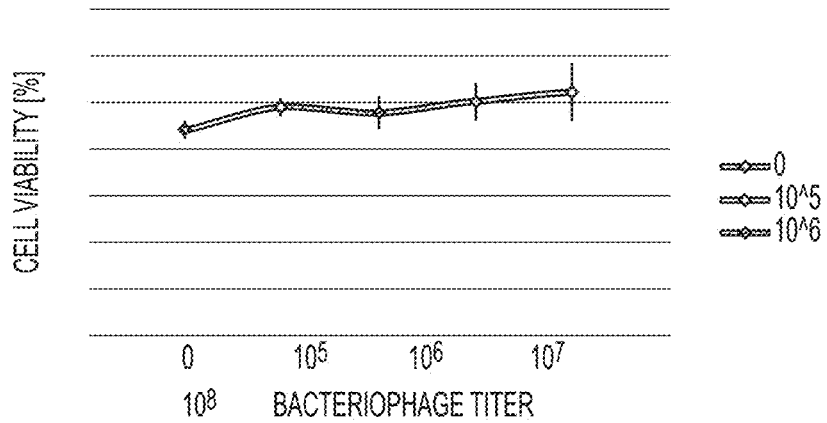
Figure 6:
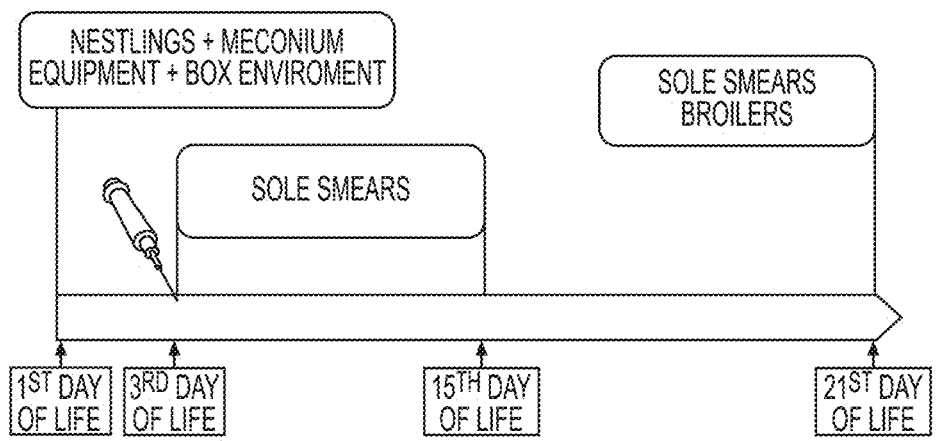
Figure 7:
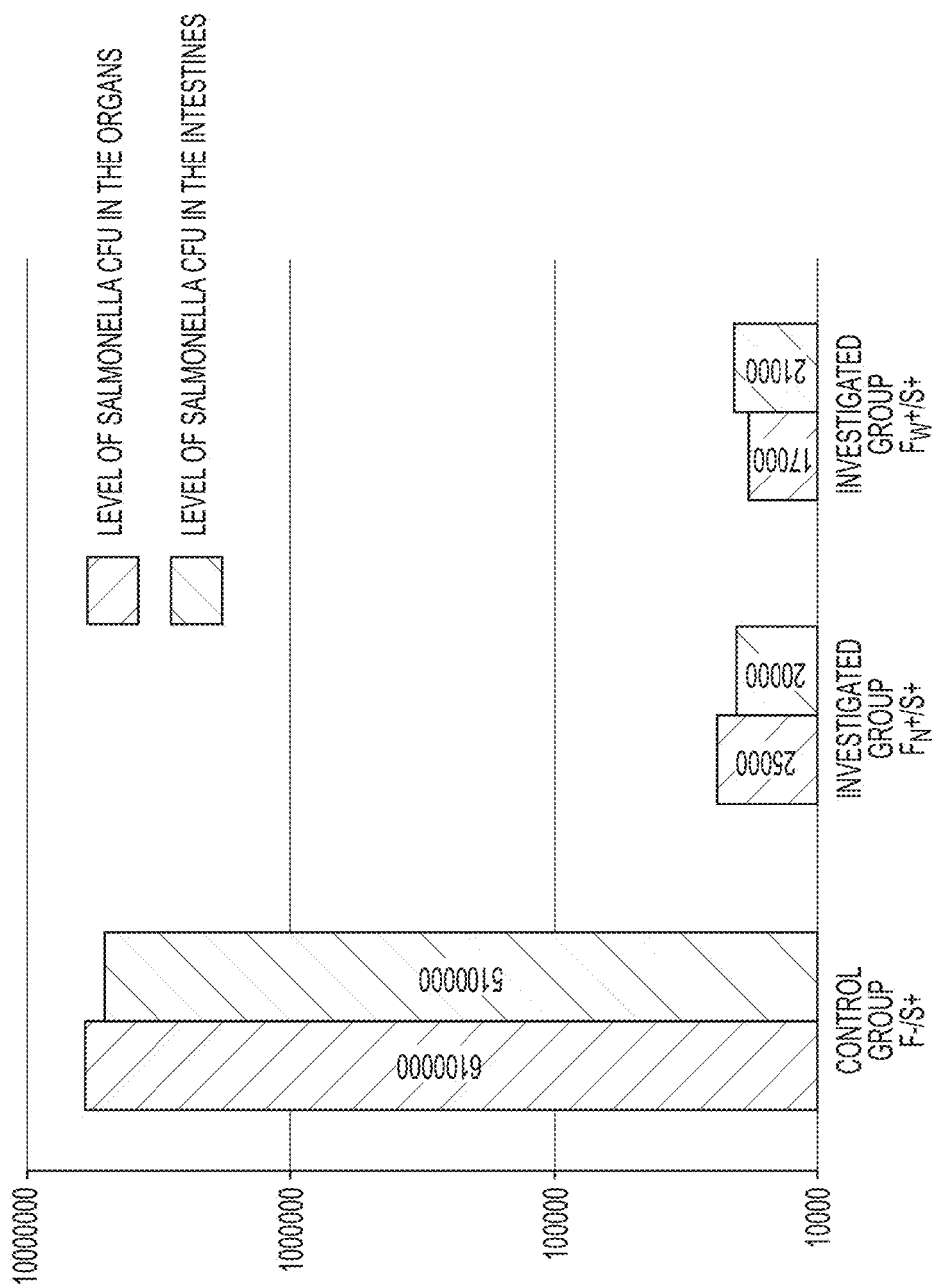

In order to clarify the invention, it has been illustrated in the accompanying figures which present:

FIG. 1: The restriction profiles for selected bacteriophages;

FIG. 2: The graphs of the monitored parameters of the conducted experiments;

FIG. 3: Sample image of ELISA plates immediately after adding the reaction mixture and after three hours of incubation. The OD600 optical density of the used suspension of *S. enterica* ser. Enteritidis ATCC 13076 strain amounting to 0.05, 0.1, 0.25, 0.5, 1.0 and 2.0, respectively corresponds to the density of cells—$8\times10^5$, $1.05\times10^6$, $7.0\times10^6$, $3.5\times10^7$, $1.4\times10^8$ and $3.8\times10^8$;

FIG. 4: The results of thermal stability of selected bacteriophages carried out within three months in three different temperature conditions;

FIG. 5: Results of bacteriophage preparation's cytotoxicity testing with neutral red method. A preparation containing a sterile mixture of bacteriophages was added for 24 h to culture of mouse 3T3 fibroblasts, and cell viability was assessed with the use of neutral red uptake test;

FIG. 6: Detection of *Salmonella bacilli* in the experiment which was carried out;

FIG. 7: The level of CFU *Salmonella* in internal organs and intestines of 21-day-old chicks.

The herein description has been supplemented with the following examples which serve for better illustration of the nature of the invention. However, these examples should not be identified with the full scope of the invention.

EXAMPLE 1

Isolation and Description of Bacteriophages

Establishing a Bank of *Salmonella* Strains (Serovars) Most Frequently Isolated from Humans and Farm Animals The set of 108 *Salmonella* ssp. strains, consisting of the most frequently isolated serovars, was collected for the necessity of the project (Table 1). These strains are applied in determination of specificity of purified bacteriophages. The collection is comprised of both reference strains available in public repositories, as well as isolates obtained owing to cooperation with the VETLAB company (Brudzew, Poland) and State Sanitary Inspection.

TABLE 1

The list of *Salmonella enterica* serovars and their origins.

| No. | Serovar | Number of strains | Source |
| --- | --- | --- | --- |
| 1 | Berta | 1 | VetLab |
| 2 | Brandenburg | 1 | State Sanitary Inspection |
| 3 | Coeln | 1 | VetLab |
| 4 | Colindale | 1 | VetLab |
| 5 | Derby | 1 | VetLab |
| 6 | Enteritidis | 1 | ATCC |
|   |   | 1 | State Sanitary Inspection |
|   |   | 58 | VetLab |
| 7 | Gallimarum Pullorum | 1 | VetLab |
| 8 | Hadar | 2 | VetLab |
|   |   | 1 | State Sanitary Inspection |
| 9 | Heidelberg | 1 | VetLab |
| 10 | Infantis | 6 | VetLab |
|   |   | 1 | State Sanitary Inspection |
| 11 | Mbandaka | 1 | VetLab |
| 12 | Moscow | 1 | VetLab |
| 13 | Newport | 5 | VetLab |
| 14 | Paratyphi | 1 | ATCC |
| 15 | Senfenberg | 1 | VetLab |
| 16 | Typhi | 1 | ATCC |
| 17 | Typhimurium | 1 | ATCC |
|   |   | 1 | State Sanitary Inspection |
|   |   | 10 | VetLab |
| 18 | Virchow | 9 | Vetlab |

Isolation of Bacteriophages, from Environmental Samples, Showing Activity Towards Selected Serovars of Reference *Salmonella* ssp Strains Bacteriophages were isolated from samples provided by the Wastewater Treatment Plants from Lodz, Poland and Tuszyn, Poland. The studies confirmed that the samples collected from sands' separation stage (sand chamber), which is one of the wastewater's treatment processes, are the richest source of viruses. Moreover, the bacteriophages were also obtained from hen feces, provided by a private farmer and VETLAB company specializing in bacterial contamination analysis of farms. Isolation of phages was carried out with the use of *Salmonella enterica* reference strains, including Typhimurium, Enteritidis and Typhi serovars, as well as several environmental strains. So far, several selected phages were described in details (Table 2).

TABLE 2

The list of obtained bacteriophages and their host strains.

| No. | Bacteriophage | Source | Host strain |
| --- | --- | --- | --- |
| 1 | 1st1 | Wastewater treatment plant | *S. enterica* ser. Typhimurium LT2 |
| 2 | 1sent3 | Wastewater treatment plant | *S. enterica* ser Enteritidis ATCC 13076 |
| 3 | 1sent4 | Wastewater treatment plant |  |
| 4 | 3sent1 | Wastewater treatment plant |  |
| 5 | 4sent1 | Private farm |  |
| 6 | 6sent1 | Private farm |  |
| 7 | 5sent1 | VetLab | *S. enterica* ser. Enteritidis 65/S/10 |
| 8 | 8sent65 | VetLab |  |
| 9 | 8sent1748 | VetLab | *S. enterica* ser. Enteritidis 1748 |
| 10 | 2styp4 | VetLab | *S. enterica* ser. Typhi ATCC 13311 |
| 11 | 2styp5 | VetLab |  |
| 12 | 6styp1 | Private farm |  |

All phages intended for further investigations were purified with the use of the screening method in order to obtain a single plaque on the LB (Luria-Bertani) plates. This procedure required at least five time application of the screening process.

Initially, specificity of viruses isolated with the use of the plate method was defined by determining the lytic capability of isolated bacteriophages towards 17 selected *S. enterica* strains, including 7 various serovars selected, 9 strains of Enteritidis serovars isolated from humans and farming animals, as well as the host strains of analyzed bacteriophages (Table 3). In order to confirm the results, the specificity determination of isolated bacteriophages was repeated three times.

TABLE 3

Specificity of selected bacteriophages in relation to chosen reference and environmental strains.

| *S. enterica* serovars | Bacteriophage | | | | | | | | | | | |
| --- | --- | --- | --- | --- | --- | --- | --- | --- | --- | --- | --- | --- |
|  | 1st1 | 1sent3 | 1sent4 | 3sent1 | 4sent1 | 5sent1 | 6sent1 | 8sent65 | 8sent1748 | 2styp4 | 2styp5 | 6styp1 |
| Typhimurium LT2 | + | − | − | + | − | + | − | + | + | − | − | + |
| Typhimurium 1751 | − | − | + | − | − | − | − | + | − | − | − | − |
| Typhi ATCC 13311 | + | − | − | + | − | + | − | + | + | + | + | + |
| Paratyphi A ATCC 19150 | − | − | + | − | − | − | − | + | − | − | − | + |
| Infantis 789 | − | − | − | − | − | − | − | − | − | − | + | − |

TABLE 3-continued

Specificity of selected bacteriophages in relation to chosen reference and environmental strains.

| S. enterica serovars | Bacteriophage | | | | | | | | | | | |
|---|---|---|---|---|---|---|---|---|---|---|---|---|
| | 1st1 | 1sent3 | 1sent4 | 3sent1 | 4sent1 | 5sent1 | 6sent1 | 8sent65 | 8sent1748 | 2styp4 | 2styp5 | 6styp1 |
| Brandenburg 584 | + | − | + | + | − | + | − | + | + | − | − | − |
| Hadar 817 | + | − | − | + | − | − | − | + | + | − | − | − |
| Enteritidis D ATCC 13076 | + | + | + | + | + | + | + | + | + | − | − | + |
| Enteritidis 1748 | + | + | + | + | − | + | − | + | + | − | − | − |
| Enteritidis 65/S/10 | + | − | + | + | − | + | + | + | + | + | + | − |
| Enteritidis 249 | + | + | + | + | + | + | nd | + | + | − | − | nd |
| Enteritidis 1014/S/09 K-1 | + | + | + | + | − | + | nd | + | + | − | − | nd |
| Enteritidis 1192/S/09 K-8 | + | − | + | + | − | + | nd | + | − | − | − | nd |
| Enteritidis 1250/S/09 | + | − | + | + | − | + | nd | + | + | − | − | nd |
| Enteritidis 1446/S/09 K-31 | + | + | + | + | − | + | nd | + | + | − | − | nd |
| Enteritidis 1535/S/09 | + | + | + | + | + | + | nd | + | + | − | − | nd |
| Enteritidis 2050/S/09 K-4 | + | + | + | + | + | + | nd | + | + | − | − | nd | nd—not determined

The resulting phages, propagated in the host strain, were concentrated by PEG8000. Such prepared samples were subjected to the process of isolation of genomic DNA of studied bacteriophages. This procedure uses zircon spheres of 0.1 mm diameter. It also uses extraction with organic solvents and commercial systems for the isolation of genomic DNA. The resulting DNA is used in (1) restriction analysis (three independent experiments using the EcoRI enzyme) generating various restriction profiles for different bacteriophages, which represents an initial gene characterization of phages (FIG. 1).

A more detailed genetic characterization is obtained from sequencing the genomes of bacteriophages from our collection, performed with the use of new-generation sequencing techniques, subcontracted to the Macrogen company. Analysis of the results of such sequencing is performed by our research team. It was established that so far obtained sequences of the genomic DNA show high homology towards the bacteriophage from very well explored T5 family and are the lytic bacteriophages.

EXAMPLE 2

Manufacture of the Preparation

Determination and Optimization of Bacteriophage Propagation Process Conditions in a *Salmonella* ssp. Culture at a Laboratory Scale Optimization was carried out with the use of *Salmonella enterica* ser. Enteritidis ATCC 13076 strain. The parameters taken into consideration were as follows: inoculum volume of a bacterial culture and bacteriophages, time of the pure culture process and incubation of infected culture, temperature of the culture, aeration level, pH of medium and conditions required for lytic cycle induction.

The optimal inoculum volume of bacterial culture was assessed to be $2\times10^9$ CFU for 0.5 l of culture medium. The optimized culture process was being carried out until optical density reached the level of $OD_{600}=0.5$, which was achieved after 3 hours of incubation. The temperature of 37° C. appeared to be the optimal for bacterial growth. The optimal aeration level was achieved by shaking at 220 rpm in the New Brunswick shaker. The optimal culture's growth was observed on the LB medium of pH=7.0. The optimization process demonstrated that the addition of 10% of bacteriophage suspension showing titer of $10^9$ (50 ml per 500 ml of culture) is the most favourable inoculum amount. Also, the analysis showed that the optimal initial proportion of bacteriophages particles and bacterial cells is 25:1. Moreover, the optimization studies revealed that the isolated bacteriophages display lytic nature and consequently induction of the lytic cycle is not required.

The process of bacteriophage's recovery from culture was performed by ultracentrifugation in Beckman L-80 type ultracentrifuge. Bacterial cultures infected with bacteriophages after proper incubation process (see above) were initially centrifuged for 30 min (3700 g). Afterwards, the supernatant was transferred into Beckman type ultracentrifugation tubes and ultracentrifuged for 2 hours (200 000 g). This procedure allowed for simultaneous purification and concentration of phage preparation.

Optimization of *Salmonella* spp Reference Strain Culture in 10-Liters Scale

In the next step of the optimization, bacteriophage propagation method in a 10-liters bioreactor (8-liters of working volume) was developed. For this purpose, 8 liters of LB medium was prepared and autoclaved (for 20 min. at 120° C.) in the bioreactor. Before inoculation with 200 ml of *Salmonella* Enteritidis 65 strain, the medium was aerated to 90%-100% and heated up to 37° C. The inoculum was a 16-hour bacterial culture showing optical density of approximately $OD_{600}=5.0$ ($4.5-5*10^9$ CFU/ml). After inoculation of the medium, sample was taken in order to measure optical density ($OD_{600}$) of *Salmonella* Enteritidis 65 initial culture.

The crucial parameters of the culture and the final titer of propagated bacteriophages were monitored (Table 4 and 5). The culture was carried out in bioreactor with constant aeration at 1.3 lpm (air volume delivered to the medium during 1 minute) and stirring at 50 rpm. After 40 minutes of the process, stirring intensity was increased from 50 to 100 rpm. During the culture process, samples were taken every 30 minutes for determination of optical density of the culture ($OD_{600}$). When the bacterial culture's optical density ($OD_{600}$) of the value of 0.48-0.55 was achieved, a 3sent1 bacteriophage suspension of suitable titer was added into the culture, in the volumes as follows:

800 ml in case of experiment 1,
700 ml in case of experiment 2, as well as
200 ml in case of experiment 3 and 4.

From this point of time, the culture was carried out for 4 hours with constant aeration and stirring (see above). The changes of optical density and phage propagation kinetics were monitored by taking samples every hour. During the process, culture parameters, including pH, $pO_2$ (aeration level indicated in %), temperature of the medium and correct level of stirring, were monitored. Every monitored parameter was recorded with the use of software designed for documentation of the course of culture process (FIG. 2), except experiment 1, due to technical problems experienced with initializing of the software. During the conducted experiments, progressing decrease of dissolved oxygen level in medium (increase of oxygen consumption by bacterial cells due to their growth in the culture), as well as small pH fluctuations within the range of 7.2-6.7, were noted.

Regardless of the phage suspension volume used (from 200 to 800 ml with titer of 1.3-2.3×10$^9$ PFU/ml), high propagated bacteriophage titer of about 10$^9$ PFU/ml was achieved.

TABLE 5

Parameters of 3sent1 phage's propagation in 10 liters of *Salmonella* Enteritidis 65 strain culture.

| | Volumes applied [ml] | | | |
|---|---|---|---|---|
| | Experiment 1 | Experiment 2 | Experiment 3 | Experiment 4 |
| Bacterial inoculum | 200 ml | 200 ml | 200 ml | 200 ml |
| Phage suspension | 800 ml | 700 ml | 200 ml | 200 ml |
| | $OD_{600}$ | | | |
| Beginning of the process | 0.097 | 0.089 | 0.070 | 0.070 |
| Before addition of phage suspension | 0.488 | 0.501 | 0.501 | 0.535 |
| 1h of phage's propagation | 0.589 | 0.720 | 0.856 | 0.477 |
| 2h of phage's propagation | 0.150 | 0.286 | 0.632 | 0.198 |
| 3h of phage's propagation | 0.110 | 0.210 | 0.372 | 0.160 |
| 4h of phage's propagation | 0.068 | 0.182 | 0.320 | 0.166 |

TABLE 5

Number of propagated 3sent1 phage particles.

| | Density of phage suspension [PFU/ml] | | | |
|---|---|---|---|---|
| | Experiment 1 | Experiment 2 | Experiment 3 | Experiment 4 |
| Initial phage suspension | 2.32 × 10$^9$ PFU/ml | 1.17 × 10$^9$ PFU/ml | 1.33 × 10$^9$ PFU/ml | 1.44 × 10$^9$ PFU/ml |
| 1h of phage's propagation | 6.20 × 10$^9$ PFU/ml | 1.05 × 10$^9$ PFU/ml | 1.42 × 10$^9$ PFU/ml | 4.94 × 10$^9$ PFU/ml |
| 2h of phage's propagation | 5.54 × 10$^9$ PFU/ml | 4.32 × 10$^9$ PFU/ml | 5.98 × 10$^9$ PFU/ml | 3.90 × 10$^9$ PFU/ml |
| 3h of phage's propagation | 6.26 × 10$^9$ PFU/ml | 3.84 × 10$^9$ PFU/ml | 5.72 × 10$^9$ PFU/ml | 5.80 × 10$^9$ PFU/ml |
| 4h of phage's propagation | 7.94 × 10$^9$ PFU/ml | 4.16 × 10$^9$ PFU/ml | 4.26 × 10$^9$ PFU/ml | 3.16 × 10$^9$ PFU/ml |

After 4 hours of bacteriophage propagation process, the whole content of bioreactor was centrifuged for 30 minutes at 4° C., at the speed of 4500 rpm/min. Since the technical parameters applied are not effective enough for precise separation of biomass from medium; at the next step the supernatant containing phage particles was micro-filtrated twice with the use of the filtration cross-flow system with membrane cassettes for separation of remaining biomass and sterilization of the obtained phage preparation CONCLUSIONS: The performed biotechnological processes enabled us to describe initial restrictions for phage particles propagation method using *Salmonella* spp strain culture in 10-liters bioreactor scale.

Volume of medium—8 liters;
Volume of *Salmonella* Enteritidis 65 inoculum ($OD_{600}$=5; 4.5-5×10$^9$ CFU/ml)—200 ml;
Volume of phage suspension (titer 10$^9$ PFU/ml)—200 ml;
Time of phage particles propagation process—3 hours;
Parameters of centrifugation—30 minutes at 4° C., at the speed of 4500 rpm/min;
Two-time microfiltration (membrane with pore size of 0.22 μm);
Titration procedure of the obtained phage preparation;
Development of the Preparation's Manufacturing and Purification Technology
Stages of Bacteriophage Preparation's Manufacturing Process 1. Bioreactor Culture.

Propagation process of bacteriophage particles is the first stage of the production line. This is realized by inoculating a bacterial culture of *Salmonella* in a bioreactor (conditions described above) with bacteriophage particle suspension. During the culture process, phage particles are propagated in bacterial cells leading to cell lysis. Each of all three bacteriophages has to be propagated in a separate culture. So far in our research, a classic 10-liter bioreactor (8 liters of working volume) has been used. In order to carry out this type of culture, previously prepared components are used, including (1) bacterial inoculum and (2) bacteriophage suspension which is added after achieving a suitable optical density ($OD_{600}$) of the bacterial culture. After addition of phage suspension, the culture is carried out from 3 to 4 hours and the process enables to obtain a high titer of a propagated bacteriophage at the level of about 10$^9$ PFU/ml. Once the propagation procedure is finished, the culture is transferred in a sterile manner to the next stage of production process by means of peristaltic pump. In the future, 100-liter bioreactors or single-use advanced bioreactor bags (up to 15 liters), which lately successfully replace classic bioreactors, are planned to be applied at the production line.

2. Removal of Biomass.

Since the total lysis of bacterial culture during the bioreactor incubation process is not possible, a subsequent stage separation of the biomass from phage-containing culture liquid is required. Therefore, at the first stage, the culture is transferred to a centrifuge, and then microfiltration process is carried out twice using cross-flow filtration system containing membrane with pore size of 0.22 µm. This procedure allows to obtain a sterile bacteriophage suspension with very small decrease in phage particles titer. Once the filtration process is finished, the suspension is transferred in a sterile manner to the next stage of production process by means of peristaltic pump. In the future, expansion of this stage of the production line by purchasing additional filtration systems is planned. This would allow for treatment of the biological material obtained from a single bioreactor culture without the need for cleaning and sterilization of the filtration equipment used during this stage.

3. Product Concentration (Optional).

Depending on the product demand, bacteriophage suspension can be concentrated 10-fold which allows for increase of the number of phage particles in a given volume. Therefore, a cross-flow filtration system with ultra-filtration membrane of 30 or 50 kD cut-off (depending on the phage), is used. This process allows for 7.5-fold concentration of bacteriophage particles.

4. Removal of Potential Endotoxin Contamination.

In order to eliminate endotoxin remaining after lysis of bacterial cells induced by bacteriophages during the biotechnological process, application of special adsorption columns is planned. These columns will contain resin suitable for removing endotoxin of size and capacity depending on the volume of the phage-containing preparation.

5. Preparation of the Product in Liquid Phase.

At this stage, a mixture of different bacteriophage suspensions, obtained in procedures described above, is prepared. The mixture should contain all bacteriophages with very similar titer value. Bacteriophages selected for the preparation show lysis capability of widest spectrum of *Salmonella* spp bacterial strains from the possessed collection. Subsequently, the preparation is portioned in strictly sterile conditions. Additionally, during this process the final suspension is again subjected to sterilization by means of a single-use, micro-filters (0.22 µm).

6. Microencapsulation (Optional)

Depending on whether the product is required in liquid or solid form, implementation of microencapsulation technology is planned in order to enclose bacteriophage particles in alginate capsules. The purpose of this stage is to generate easily absorbable capsules which safely pass through the digestive system and to release gradually the enclosed bacteriophage particles in the target place without irritating the whole organism.

EXAMPLE 3

Research of the Effectiveness and Safety of the Preparation In Vitro Research

Development and Optimization of the Highly Efficient and Automated Colorimetric Method for Measurement of Bacteriophage Preparation Activity The commercially available alamarBlue® reagent was used for development of the assay useful for measuring the bacteriophage lytic activity. The alamarBlue® is an indicatory dye which enables fast and accurate quantification of proliferation and cytotoxicity based on chromatic reaction. An easy-to-use reagent takes advantage of the phenomenon of a reduction-oxidation reaction (REDOX) and during the process a resazurin changes its colour from blue (non-fluorescent) to red (fluorescent) as a result of oxidation, which is a consequence of cell metabolic activity. The change of colour is visible with the naked eye. It can be also measured spectrophotometrically or fluorometrically. Due to its lack of cell toxicity, alamarBlue® is especially valuable in observation of bacterial cell differentiation in microbial cultures. This test was adjusted for application on 96-well ELISA plate and two techniques of measurement were elaborated. The first one was intended to assess the lytic activity of bacteriophages. During the test, the so called fresh working mixture was used (prepared just before application on the ELISA plate), which consisted of alamarBlue® and 20% sterile Tween™ 80 solution (3 parts of alamarBlue® and 1 part of 20% sterile Tween™ 80 solution), and was added to wells containing studied *Salmonella* strain suspension of appropriate density, as well as to wells filled with both *Salmonella* cell suspension of appropriate density and studied bacteriophage suspension of desired titer. The procedure enables visual determination of the lytic activity of phage particles in relation to the investigated *Salmonella* strains. The blue colour of the reaction mixture of alamarBlue®+20% sterile Tween™ 80 solution (3 parts of alamarBlue® and 1 part of 20% sterile Tween™ 80 solution) indicates lack of growth of the studied *Salmonella* strain and high lytic effect of proper bacteriophage concentration. Colour change of the reaction mixture of alamarBlue®+20% sterile Tween™ 80 solution (3 parts of alamarBlue® and 1 part of 20% sterile Tween™ 80 solution) from blue to red, caused by the oxidation associated with metabolic activity, indicates growth of *Salmonella* cells and lack or low lytic effect of proper bacteriophage concentration in relation to the investigated *Salmonella* strain.

A detailed experimental protocol enabling quantitative assessment of the lytic activity of bacteriophages, as well as a drawing presenting the results of a selected experiment conducted for the 3sent1 bacteriophage in relation to *Salmonella enterica* ser. Enteritidis ATCC 13076 strain (FIG. 3), are presented below.

1. Add 100 µl of *Salmonella* spp. culture suspension of proper optical density ($OD_{600}$) relating to appropriate number of colony forming units (CFU/1 ml)[1] into each well of the first row in columns from 1 to 12. In detail: suspension of the optical density of 0.05, 0.1, 0.25, 0.5, 1.0 and 2.0 into the plate wells: 1 and 7, 2 and 8, 3 and 9, 4 and 10, 5 and 11, as well as 6 and 12, respectively.
2. Add 100 µl of phage suspension at concentration of $6.5 \times 10^9$ PFU (plaque forming units) into each well of the first row in columns from 1 to 6. The volume proportion of bacterial to phage suspension is 1:1.
3. Similarly, add 75 µl of *Salmonella* spp. culture suspension of proper optical density and 125 µl of phage suspension into wells of the second row. The volume proportion of bacterial to phage suspension is 1:1.5.
4. Similarly, add 50 µl of *Salmonella* spp. culture suspension of proper optical density and 150 µl of phage suspension into wells of the third row. The volume proportion of bacterial to phage suspension is 1:3.
5. Prepare the controls; add sterile LB medium instead of phage suspension into each well of the first, second and third row in columns from 7 to 12 (control of *Salmonella* strain growth of given densities). Additionally, add phage suspension into each well of $6^{th}$, $7^{th}$ and $8^{th}$ row in column 3 (control of phage suspension contamination) and add LB medium into each well of $7^{th}$ and 8th row in column 7 (control of contamination of the medium applied to dilute the culture in investigated and control set).

6. Cover the ELISA plate with sterile lids and incubate for 4 h at 37° C. After the incubation stage, add 50 µl of alamarBlue®+20% sterile Tween™ 80 reaction mixture[2] into each well plate. Due to the reaction mixture's susceptibility to light, protect the plate with aluminium foil. Continue the incubation for the next 3 h in 37° C. Perform visual observation every 30 minutes.

[1] Relation between the $OD_{600}$ optical density and the CFU value should be determined experimentally in several independent approaches.
[2] The mixture should be prepared directly before application into wells on ELISA plate (3 parts of alamarBlue® and 1 part of 20% sterile Tween™ 80 solution).

The modified protocol may be applied as a useful tool for estimation of protective effect of bacteriophages against *Salmonella* Enteritidis growth. Colour change of the reaction mixture of alamarBlue® from blue to red, which is caused by the oxidation associated with metabolic activity, indicates *Salmonella* cells' growth. The blue colour of the reaction mixture of alamarBlue®+20% sterile Tween™ 80 solution indicates protective effect of phage suspension preventing growth of *Salmonella* cells. The detailed protocol:

1. Add 20 ml of LB medium to 100 ml Erlenmayer conical, flat-bottom flasks and autoclave.
2. Inoculate 20 ml of sterile LB liquid medium with *S. Enteritidis* strain and incubate the culture overnight at 37° C. with shaking (rpm=150). The suspension shall be stored in refrigerator at 4° C. not longer than for 1 week and treated as inoculum for current cultures.
3. Inoculate 20 ml sterile LB liquid medium (in 100 ml Erlenmayer flasks) with 20 µl of *S. Enteritidis* strain and incubate the culture for 1 h at 37° C. with shaking (rpm=150).
4. Make appropriate dilutions of the suspension in LB. Dilutions should contain 2000, 200 and 20 bacterial cells in 1 ml. Use for experiments with phage suspension showing protective effect.
5. Mix 100 µl of the appropriate dilution of *S. Enteritidis* bacterial cells with 100 µl of bacteriophage suspension and add the mixtures into the sequential wells of 96-wells titer plate.
6. Prepare the controls; appropriate dilutions of *S. Enteritidis* suspension which will serve as bacterial growth control, as well as the bacteriophage suspension and a clear LB medium as the controls of microbial contamination.
7. Cover the titer plate with a lid and incubate for 4 h at 37° C.
8. Cover the titer plate with a lid and protect with aluminium foil against admission of light, then continue the incubation for next 4 h at 37° C. Perform the reading, after 4 hours of the incubation process.

Research of Thermal Stability of Bacteriophages

Analysis of thermal stability of bacteriophages storage was carried out for 3 months at three different temperatures: −20° C., +4° C. and at room temperature. The stability was measured by determining phage titer by means of plate count at the beginning of the experiment, after one month and after three months of storage in the mentioned above temperatures. Bacteriophages were suspended in LB medium after propagation and purification from bacterial cells. The results indicate that some of bacteriophages of the existing collection, namely 3sent1, 8sent65 and 8sent1748 (FIG. 4), retain their title at the order of magnitude within three months of storage at −20° C. or 4° C., contrary to other phages, e.g.: 1st1 or 2styp5 (FIG. 4), which is important in view of durability.

Research of Bacteriophage Preparation's Safety
Determination of Endotoxin Level

Determination of endotoxin concentration (LPS), the major component of cell's wall of gram negative bacteria, was performed using LAL test (Limulus Amebocyte Lysate). The LAL tests are available as ready-to-use kits for colorimetric measurement of LPS level and activity:

1. Kit produced by Genscript (ToxinSensor LAL Endotoxin Assay Kit).
2. Kit produced by LONZA (QCL-1000 Endpoint chromogenic LAL Assay).

In these tests, LAL reagent interacts with endotoxin in analyzed samples resulting in production of a reaction product which is able to react with chromogenic substrate, thus the spectrophotometric measurement is possible. The intensity of the colour is directly proportional to endotoxin concentration.

Phage-containing samples were taken at different stages of the technological process (assessment of ultracentrifugation's effectiveness—A1-A2 samples, and phage particles concentration using different membranes cut-off: 100 kDa—B1-B5 samples and 50 kDa—C1-C7 samples) and analyzed for endotoxin level. The results obtained indicate presence of high amount of LPS in samples taken after the phage particles concentration stage (Table 6).

TABLE 6

Results of LPS concentration in analyzed samples.

| Sample No. | Description | LPS concentration EU/ml |
|---|---|---|
| A1 | Sample containing pellets (phages) after ultracentrufugation suspended in SM buffer | >$10^6$ |
| A2 | Sample contaning supernatant after ultracentrifugation | 106 345 |
| B1 | Initial sample —medium contaning phages after seperation of bacterial cells and sterilization | >$10^6$ |
| B2 | 10-fold concentrated preparation (retentate) | 156 389 |
| B3 | Permeate—liquid filtered through a concentration membrane | 4 888 |
| B4 | Saline used to flush the membrane after the end of filtration process, collected as permeate | 55 |
| B5 | Saline used to flush the membrane after the end of filtration process, collected as retentate | 0.5 |

TABLE 6-continued

Results of LPS concentration in analyzed samples.

| Sample No. | Description | LPS concentration EU/ml |
|---|---|---|
| C1 | Initial sample—medium contaning phages after seperation of bacterial cells and sterilization | 211 327 |
| C2 | Permeate—liquid filtered through a concentration membrane | 25 |
| C3 | 10-fold concentrated preparation (retentate) | $1.36 \times 10^{10}$ |
| C4 | Saline used to flush the membrane after the end of filtration process, collected as retentate (first sample 100 ml) | $1.69 \times 10^{9}$ |
| C5 | Saline used to flush the membrane after the end of filtration process, collected as retentate (second sample 200 ml) | $1.32 \times 10^{9}$ |
| C6 | Saline used to flush the membrane after the end of filtration process, collected as retentate (third sample 200 ml) | $1.05 \times 10^{8}$ |
| C7 | Saline used to flush the membrane after the end of the filtration process, collected as retentate (fourth sample 500 ml) | 1 549 |

Cytotoxicity Analysis

Investigation was carried out by means of the neutral red uptake assay. The test was performed with 96-wells plates using 3T3 cell line. 3T3 cells are mouse-derived, not-transformed fibroblasts conventionally used for in vitro toxicity analysis. Analysis was carried out on the preparation containing a mixture of three different phages in 4 serial dilutions. Measurements were performed in duplicates and in 5 independent repetitions. Obtained absorbance values were used for calculation of % of cells' viability by comparing the absorbance of analyzed sample with absorbance of control sample (i.e. cells incubated in culture medium) (FIG. 5).

Cytotoxicity test using 3T3 cell line:
1. Put 10 000 3T3 fibroblasts suspended in standard culture medium to each well of 96-wells plate and incubate for 24 hours in the incubator (37° C.; 5% $CO_2$).
2. Remove culture medium and add bacteriophage preparation diluted in culture medium. Continue the incubation for next 24 hours (37° C.; 5% $CO_2$).
3. After the incubation, remove medium containing phage preparation, wash the monolayer of PBS fibroblasts and incubate with neutral red solution in PBS for 3 hours (37° C.; 5% $CO_2$).
4. Remove neutral red solution, wash with PBS and induce cell lysis. Measure the amount of absorbed dye by colorimetric method.

Obtained results indicate lack of cytotoxic activity of bacteriophage preparation even at high concentrations. Consequently, acute cytotoxicity is not expected to appear after using this preparation in vivo at phage concentration of at least up to $10^8$ particles.

In Vivo Research

Determination of Effectiveness and Safety of Prototype Bacteriophage Preparation Applied Against Salmonellosis in Chicken Broilers.

The study was carried out in cooperation with the University of Warmia and Mazury, as well as VETLAB.

Purpose: To evaluate the possibility of using bacteriophages in protection against salmonellosis infections in broiler chickens.

*Salmonella enterica* ser. Enteritidis 65/S/10 strain provided by VETLAB was used to infect broilers, whereas to prepare the bacteriophage agent, three bacteriophages: 3sent1, 8sent65, and 8sent1748, isolated from two *Salmonella* enterica strains (Table 3) and showing a wide spectrum of specificity against different *Salmonella* serovars, as well as against investigated Enteritidis strains, were used. Based on specificities of the used bacteriophages, specificity of the complete preparation can be assumed (Table 7). Bacteriophage preparation was prepared in the following manner: each of the three bacteriophages were subjected to the optimized procedure of propagation, and afterwards the obtained phage suspensions were mixed, so that their titer values in the final product were similar. Two mixtures with different phage concentrations were prepared: high concentration containing $2.0 \times 10^8$ PFU/ml and low concentration containing $2.0 \times 10^6$ PFU/ml. Afterwards, the mixtures were portioned and sterilized using microfiltration. Analysis of microbial contamination showed no presence of bacteria in the bacteriophage preparation used.

TABLE 7

Assumed specificity of the preparation based on specificity of phages included.

| Serovar | Strain | 3sent1 | 8sent1748 | 8sent65 | PREPARATION |
|---|---|---|---|---|---|
| Typhimurium | LT2 | + | + | + | + |
| | 1751 | − | + | − | |
| Typhi | ATCC 13311 | + | + | + | + |
| Paratyphi | A ATCC 19150 | − | + | − | |
| Infantis | 789 | − | − | − | |
| Brandenburg | 584 | + | + | + | + |
| Hadar | 817 | + | + | + | + |
| Enteritidis | D ATCC 13076 | + | + | + | + |
| | 1748 | + | + | + | + |
| | 65/S/10 | + | + | + | + |
| | 249 | + | + | + | + |
| | 1014/S/09 K-1 | + | + | + | + |
| | 1192/S/09 K-8 | + | + | − | |
| | 1250/S/09 | + | + | + | + |
| | 1446/S/09 K-31 | + | + | + | + |
| | 1535/S/09 | + | + | + | + |
| | 2050/S/09 K-4 | + | + | + | + |
| | Farm "K" K-3 | + | + | + | + |
| | Farm "K" K-6 | + | + | + | + |
| | Farm "K" K-9 | + | − | − | |
| | Farm "K" K-10 | + | + | − | |
| | Farm "K" K-11 | + | − | − | |
| | Farm "K" K-12 | + | − | − | |
| | Farm "K" K-14 | + | + | + | + |
| | Farm "K" K-18 | − | − | − | |
| | Pac K-ground | − | + | + | |
| | Pac K-floor | + | + | + | + |
| | W/K-6 | + | + | + | |
| | W/K-7 | + | + | − | |
| | W/K-9 | + | + | + | + |
| | 64/S/10 | + | + | + | + |
| | 65/S/10 | + | + | + | + |

TABLE 7-continued

Assumed specificity of the preparation based on specificity of phages included.

| Serovar | Strain | 3sent1 | 8sent1748 | 8sent65 | PREPARATION |
|---|---|---|---|---|---|
| | 517/S/09 | + | + | + | + |
| | 571/S/09 | + | + | + | + |
| | 833/S/09 | + | + | + | + |
| | 838/S/09 | + | − | + | |
| | 838/S/09 B | + | + | + | + |
| | 847/S/09 | + | + | + | + |
| | 848/S/09 | + | − | − | |
| | 865/S/09 | + | + | + | + |
| | 866/S/09 | + | + | + | + |
| | 945/S/09 | + | + | + | + |
| | 975/S/09 | + | + | + | + |
| | 1013/S/09 K-4 | + | + | + | + |
| | 1021/S/09 | + | + | + | + |
| | 1022/S/09 K-9 | + | + | + | + |
| | 1044/S/09 K-2 | + | − | + | |
| | 1047/S/09 K-1 | + | + | + | + |
| | 1048/S/09 K-8 | + | + | + | + |
| | 1061/S/09 K-5 | − | − | − | |
| | 1067/S/09 K-2 | + | − | − | |
| | 1067/S/09 K-3 | + | + | + | + |
| | 1085/S/09 MEK | + | + | + | + |
| | 1106/S/09 K-1 | + | + | + | + |
| | 1143/S/09 | + | + | + | + |
| | 1171/S/09 | + | + | + | + |
| | 1206/S/09 MEK | + | + | + | + |
| | 1231/S/09 | + | + | + | + |
| | 1250/S/09 | + | + | + | + |
| | 1257/S/09 K-7 | + | + | + | + |
| | 1422/S/09 MEK | + | + | + | + |
| | 1445/S/09 K-46 | + | − | + | |
| | 1465/S/09 MEK | + | + | + | + |
| | 1535/S/09 | + | + | + | + |
| | 1542/S/09 NWJ | + | + | + | + |
| | 1545/S/09 MEK | + | − | + | |
| | 1572/S/09 NWJ | + | + | + | + |
| | 1573/S/09 NWJ | + | + | + | + |
| | 1714/09 | + | + | + | + |
| | 1748 | + | + | + | + |
| | 2149/09 | + | + | + | + |
| | 2619/S/10 | + | + | + | + |

Experimental Procedure

One hundred fifty Ross 308 roosters, divided randomly into 5 equal, isolated groups (separate rooms—boxes), were used for the research. Chickens were fed with standard, complete feed produced by Agrocentrum Kolno, Poland and kept in conditions complying with recommendation of the biological material's manufacturer. Four-days-old chickens from boxes 1, 2 and 3 were infected with *Salmonella Enteritidis bacilli* in a dose of $1\times10^5$ CFU per animal (Table 8). Chickens from boxes 4 and 5 were not infected with *Salmonella bacilli*. The bacteriophage preparation was administered to chickens placed in boxes 1 (low concentration of $2.0\times10^6$ PFU/ml, marked as $F_N$), 2 and 5 (high concentration of $2.0\times10^8$ PFU/ml, marked as $F_W$). The preparation was administered to roosters once a day for first 14 days of their lives. The bacteriophage agent was not administered to chickens from boxes 4 and 5. The rearing time was 21 days and during this period only five birds from different boxes died (Table 8). Since the detected death rate was minimal and did not depend on a given group of chickens therefore the death rate could not have been the result of the administration of the phage preparation.

TABLE 8

The scheme of administration of bacteria and bacteriophages, as well as birds' viability.

| Box | *Salmonella* infection | Bacteriophage administration | Chicken's viability |
|---|---|---|---|
| 1 | $1 \times 10^5$ CFU/bird | $2.0 \times 10^6$ PFU/ml | 30/30 |
| 2 | $1 \times 10^5$ CFU/bird | $2.0 \times 10^8$ PFU/ml | 29/30 |
| 3 | $1 \times 10^5$ CFU/bird | — | 28/30 |
| 4 | — | — | 30/30 |
| 5 | — | $2.0 \times 10^8$ PFU/ml | 28/30 |

Detection of *Salmonella Bacilli*

Samples for *Salmonella bacilli* detection were collected according to the scheme described below (FIG. 6):

Investigation of feces during 21 days of experiment,

Investigation of litter—sole smears were collected on $3^{rd}$, $15^{th}$ and $21^{st}$ day of birds' life, Investigation of liver, spleen and intestines of 21-days-old broilers, Investigation of empty boxes before insertion of nestlings—smears were collected from walls, feeders, drinkers and floor (control), Investigation of one-day-old nestlings—internal organs, intestines and meconium (control).

Detection of *Salmonella bacilli*'s presence in analyzed samples was carried out by an accredited laboratory—VETLAB (Brudzew, Poland). In 2008, this laboratory received authorization of the Chief Veterinary Officer (no. GIWhig-5120-23/08) to perform detection of *Salmonella bacilli* by means of bacteriological-qualitative method.

*Salmonella bacilli* were not detected in analyzed samples of internal organs and intestines of one-day-old nestlings, meconium, as well as smears from boxes before insertion of nestlings. The lack of *Salmonella bacilli* or different level of its detection in case of analysis of feces from 21 days of experiment, as well as sole smears analysis on $3^{rd}$, $15^{th}$ and $21^{st}$ day of life (Table 9), and internal organs analysis of 21-days-old broilers (FIG. 7) was dependent on the box under investigation. That is, as it was anticipated, no *Salmonella bacilli* were detected in chickens from boxes 4 and 5. In case of birds from box 3, which were infected with *Salmonella bacilli* and not treated with the bacteriophage preparation, the *bacilli* were detected starting from sixth day of life. Whereas, in case of chickens from boxes 1 and 2, which were infected with *Salmonella bacilli* and treated with the phage agent, inhibition of bacteria propagation was clearly seen until administration of the phage preparation was stopped. What is important, the number of *bacilli* detected in internal organs and intestines of 21-days-old birds was very low in relation to chickens which were not treated with the phage preparation. Thus, bacteriophages prevent propagation of bacteria and consequently the appearance of bacteria in feces of birds infected during the experiment. Accordingly, it can be observed that bacteriophages decrease 200-fold the infection level even a week after discontinuation of phage treatment.

TABLE 9

Level of *Salmonella* bacilli's occurrence in feces during the experiment.

| | | *Salmonella* bacilli occurrence | | | | | |
|---|---|---|---|---|---|---|---|
| Day | Infection | Box 1 $F_N$+/S+ | Box 2 $F_W$+/S+ | Box 3 F−/S+ | Box 4 F−/S− | Box 5 $F_W$+/S− | Phage addition |
| 1 | | − | − | − | − | − | Yes |
| 2 | | − | − | − | − | − | Yes |
| 3 | $2.5 \times 10^3$ | − | − | − | − | − | Yes |
| 4 | | − | − | − | − | − | Yes |
| 5 | | − | − | − | − | − | Yes |
| 6 | | − | − | $1.0 \times 10^1$ | − | − | Yes |
| 7 | | − | − | + | − | − | Yes |
| 8 | | − | − | $5.3 \times 10^3$ | − | − | Yes |
| 9 | | − | − | + | − | − | Yes |
| 10 | | − | − | $1.0 \times 10^4$ | − | − | Yes |
| 11 | | − | − | + | − | − | Yes |
| 12 | | − | $3.0 \times 10^1$ | $3.5 \times 10^4$ | − | − | -Yes |
| 13 | | − | − | + | − | − | Yes |
| 14 | | − | $2.0 \times 10^3$ | $5.5 \times 10^3$ | − | − | Yes |
| 15 | | $4.1 \times 10^3$ | $1.0 \times 10^2$ | $1.5 \times 10^3$ | − | − | No |
| 16 | | + | + | + | − | − | No |
| 17 | | $2.1 \times 10^2$ | + | $3.0 \times 10^4$ | − | − | No |
| 21 | | $5.0 \times 10^2$ | $2.2 \times 10^3$ | $4.3 \times 10^4$ | − | − | No |

"−" means, no *Salmonella* bacilli were detected
"+" means that *Salmonella* bacilli were detected, but it was difficult to determine their titer Detection of Bacteriophages' Occurrence.

Samples analyzed for bacteriophage presence were collected from feces during 21 days of the experiment and from smears from all boxes before introduction of nestlings, before infection and also a day and a week after discontinuation of phage treatment. No bacteriophages were detected in internal organs. It was observed that lack of bacteriophages or different level of their detection in birds' feces (Table 10) and sole smears analyses (Table 11) depended on the given box of chicken under analysis. That is, bacteriophages were detected in feces of chickens form boxes 1, 2 and 5, which were administered the phage agent. However, their number decreased after discontinuation of the treatment, and especially in case of birds from boxes 2 and 5, where high phage concentration was used, bacteriophages were no longer detected. It is worth adding that much smaller number of bacteriophages was detected in feces from box 5 compared to feces from box 2, which can be the result of impossibility of phage's propagation due to the lack of *Salmonella* bacilli.

TABLE 10

Bacteriophage's titer level in poultry feces.

| | Bacteriophage's titer | | | | |
|---|---|---|---|---|---|
| Day | Box 1 FN+/S+ | Box 2 FW+/S+ | Box 3 F−/S+ | Box 4 F−/S− | Box 5 F+/S− |
| 1 | 0 | 0 | 0 | 0 | 0 |
| 3 | 0 | $1.8 \times 10^7$ | 0 | 0 | $5.6 \times 10^2$ |
| 10 | $8.0 \times 10^6$ | $5.5 \times 10^4$ | 0 | 0 | $5.0 \times 10^3$ |
| 15 | $1.2 \times 10^7$ | $5.0 \times 10^1$ | 0 | 0 | $8.2 \times 10^2$ |
| 17 | $1.7 \times 10^4$ | 0 | 0 | 0 | 0 |
| 21 | $5.0 \times 10^1$ | 0 | 0 | 0 | 0 |

TABLE 11

Bacteriophage's titer level in sole smears under analysis.

| | Bacteriophage's titer | | | | |
|---|---|---|---|---|---|
| Day | Box 1 FN+/S+ | Box 2 FW+/S+ | Box 3 F−/S+ | Box 4 F−/S− | Box 5 F+/S− |
| One day after discontinuation of phage treatment (15) | $1.0 \times 10^5$ | $1.0 \times 10^3$ | 0 | 0 | $2.4 \times 10^3$ |
| One week after discontinuation of phage treatment (21) | $6.5 \times 10^5$ | 0 | 0 | 0 | 0 |

Conclusions from the Investigation of the Effect of Bacteriophage Preparation on Broilers Based on the tests performed, one can conclude that the preparation is safe and efficient.
1. The preparation is safe for poultry.
2. Bacteriophages pass through the intestinal tract and reach the feces and litter.
3. Bacteriophages do not enter internal organs of the birds.
4. Bacteriophages disappear after discontinuation of administration of the preparation.
5. Bacteriophages prevent the appearance of bacteria in feces of experimentally infected birds.
6. Bacteriophages decrease 200-fold the infection level one week after discontinuation of the phage treatment.

The invention claimed is:

1. A sterile composition comprising one or more strains of bacteriophage selected from PCM F/00069 (strain 8sent1748), PCM F/00070 (strain 8sent65) and PCM F/00071 (strain 3sent1);
   wherein each of the one or more strains of bacteriophage is present in the composition at a concentration of at least $2.0 \times 10^6$ plaque forming units (PFU) per milliliter (ml) (PFU/ml); and
   wherein the composition does not comprise *Salmonella*; and wherein the composition is formulated in a microencapsulated dosage form.

2. The sterile composition according to claim 1, wherein the composition comprises the bacteriophage strains PCM F/00069 (strain 8sent1748), PCM F/00070 (strain 8sent65) and PCM F/00071 (strain 3sent1).

3. The sterile composition according to claim 1, wherein the bacteriophage present in the composition consist of bacteriophage selected from strains PCM F/00069 (strain 8sent1748), PCM F/00070 (strain 8sent65) and PCM F/00071 (strain 3sent1).

4. The sterile composition according to claim 1, wherein each of the one or more strains of bacteriophage is present in the composition at a concentration of from $2.0 \times 10^6$ PFU/ml to $2.0 \times 10^8$ PFU/ml.

5. The sterile composition according to claim 1, wherein each of the one or more strains of bacteriophage is present in the composition at a concentration of from $2.0 \times 10^6$ PFU/ml to about $10^9$ PFU/ml.

6. The sterile composition according to claim 1, wherein the titer of bacteriophage in the composition decreases by no more than 90% when the composition is stored at 4 degrees C. for three months.

7. The sterile composition according to claim 1, wherein the composition is endotoxin free.

8. The sterile composition according to claim 1, wherein the composition is formulated in a microencapsulated liquid dosage form.

9. The sterile composition according to claim 1, wherein the composition is formulated in a microencapsulated solid dosage form.

* * * * *